United States Patent
Matsubara et al.

(10) Patent No.: US 10,888,525 B2
(45) Date of Patent: Jan. 12, 2021

(54) HYPROMELLOSE ACETATE SUCCINATE AND METHOD FOR PRODUCING THE SAME

(71) Applicant: SHIN-ETSU CHEMICAL CO., LTD., Tokyo (JP)

(72) Inventors: Junichi Matsubara, Joetsu (JP); Naosuke Maruyama, Joetsu (JP); Mitsuhiro Yoshida, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 124 days.

(21) Appl. No.: 15/797,876

(22) Filed: Oct. 30, 2017

(65) Prior Publication Data
US 2018/0116968 A1     May 3, 2018

(30) Foreign Application Priority Data
Nov. 2, 2016    (JP) ............................... 2016-215357

(51) Int. Cl.
| | |
|---|---|
| *C08B 3/16* | (2006.01) |
| *A61K 9/28* | (2006.01) |
| *A61K 47/38* | (2006.01) |
| *C08B 13/00* | (2006.01) |
| *A61K 31/525* | (2006.01) |

(52) U.S. Cl.
CPC .......... *A61K 9/2866* (2013.01); *A61K 31/525* (2013.01); *A61K 47/38* (2013.01); *C08B 13/00* (2013.01)

(58) Field of Classification Search
CPC .................................. C08B 3/16; C08B 13/00
See application file for complete search history.

(56) References Cited

U.S. PATENT DOCUMENTS

| | | | |
|---|---|---|---|
| 8,207,232 B2 * | 6/2012 | Babcock ................ | A61K 9/146 424/400 |
| 2008/0262107 A1 | 10/2008 | Babcock et al. | |
| 2016/0136283 A1 | 5/2016 | Warashina et al. | |
| 2018/0105607 A1* | 4/2018 | Petermann ............ | A61K 47/38 |

FOREIGN PATENT DOCUMENTS

| | | |
|---|---|---|
| CN | 103153343 A | 6/2013 |
| CN | 105026435 A | 11/2015 |
| CN | 105597103 A | 5/2016 |
| CN | 105899542 A | 8/2016 |
| EP | 219426 A2 * | 4/1987 |
| EP | 0648487 A1 | 4/1995 |
| JP | H07-109219 A | 4/1995 |
| JP | H08-245423 A | 9/1996 |
| WO | 2011/159626 A1 | 12/2011 |
| WO | 2014/137777 A1 | 9/2014 |
| WO | 2014/137789 A1 | 9/2014 |
| WO | 2016/148975 A1 | 9/2016 |
| WO | 2016/186895 A1 | 11/2016 |

OTHER PUBLICATIONS

Mar. 27, 2018 Extended European Search Report issued in European Patent Application No. 17199574.9.
Nov. 21, 2019 Office Action issued in Chinese Patent Application No. 201711066191.1.

* cited by examiner

*Primary Examiner* — Karuna P Reddy
(74) *Attorney, Agent, or Firm* — Oliff PLC

(57) ABSTRACT

There are provided HPMCAS (hypromellose acetate succinate) having such a property that a solution of the HPMCAS in a solvent has a controlled viscosity; and a method for producing the HPMCAS. More specifically, provided are HPMCAS having such property that a solution of 10 parts by weight of the HPMCAS in 100 parts by weight of a mixed solvent having a weight ratio of methylene chloride to methanol of 1:1 has a viscosity at 20° C. of 135 mPa·s or less; and a method for producing the HPMCAS including an esterification step of adding acetic anhydride and succinic anhydride to a solution of hypromellose in glacial acetic acid in the presence of sodium acetate to obtain a reaction product mixture, wherein the succinic anhydride is added intermittently, and a precipitation step of mixing the reaction product mixture with water to precipitate the HPMCAS.

4 Claims, No Drawings

HYPROMELLOSE ACETATE SUCCINATE AND METHOD FOR PRODUCING THE SAME

BACKGROUND OF THE INVENTION

1. Field of the Invention

The invention relates to hypromellose acetate succinate and a method for producing the hypromellose acetate succinate.

2. Related Art

As an enteric polymer, hypromellose acetate succinate, which is a polymer having four types of substituents in total, is widely known, and is produced by introducing, to a cellulose skeleton, two substituents of a methyl group ($-CH_3$) and a hydroxypropyl group ($-C_3H_6OH$) to form ether structures as well as two substituents of an acetyl group ($-COCH_3$) and a succinyl group ($-COC_2H_4COOH$) to form ester structures.

The hypromellose acetate succinate (hereinafter also referred to as "HPMCAS"), which is an enteric polymer, is widely used for a solid dispersion for improving the elution of a poorly water-soluble drug, and as an enteric coating.

An enteric-coated preparation is one of important preparations, and is widely used, for example, for administration of a drug unstable in acid or for protection from the gastric mucosa. In a conventional method for producing the enteric-coated preparation, an enteric polymer is dissolved in an organic solvent and sprayed onto a drug surface to form an enteric film thereon. In consideration of environmental preservation or safety against use of the organic solvent, so-called an aqueous enteric coating method using an aqueous dispersion of a pulverized enteric polymer has been developed (JP 07-109219A). For example, an ammonia-neutralization coating method using an aqueous enteric coating liquid prepared by mixing HPMCAS as an enteric polymer and ammonia in an amount required for neutralization of about 80% by mole or more of the carboxyl groups in the HPMCAS molecule has been disclosed (JP 08-245423A).

SUMMARY OF THE INVENTION

In the typical production of an enteric-coated preparation, an enteric polymer is dissolved in a solvent and sprayed onto a drug surface to form an enteric film thereon. However, a solution having a higher viscosity is apt to form aggregates when sprayed, and the resulting coating film has insufficient uniformity, thereby failing to have an intended acid resistance. In addition, use of a large amount of an organic solvent for lowering the viscosity of the solution is unfavorable in consideration of environmental preservation or safety.

As mentioned above, the HPMCAS is required to bring a more appropriately controlled viscosity of a solution of the HPMCAS in a solvent in order to provide stable preparations.

In view of the above circumstances, an object of the invention is to provide HPMCAS bringing a controlled viscosity of a solution of the HPMCAS in a solvent; and a method for producing the HPMCAS.

As a result of intensive studies for achieving the object, the inventors have payed attention to the method of adding succinic anhydride in a reaction step for producing HPMCAS, have found that the viscosity of a solution of the HPMCAS in a solvent can be controlled by adding the succinic anhydride intermittently (in other words, in two or more stages), and have completed the invention.

In an aspect of the invention, there is provided hypromellose acetate succinate having such a property that a solution of 10 parts by weight of the hypromellose acetate succinate in 100 parts by weight of a mixed solvent having a weight ratio of methylene chloride to methanol of 1:1 has a viscosity at 20° C. of 135 mPa·s or less.

In another aspect of the invention, there is provided a coating composition comprising the hypromellose acetate succinate and a solvent.

In still another aspect of the invention, there is provided a composition comprising the hypromellose acetate succinate, a drug, and a solvent. This composition is suitable for production of a solid dispersion.

In a further aspect of the invention, there is provided a method for producing the hypromellose acetate succinate, the method comprising an esterification step of adding acetic anhydride and succinic anhydride to a solution of hypromellose in glacial acetic acid in the presence of sodium acetate to obtain a reaction product mixture, wherein the succinic anhydride is added intermittently (in other words, two or more stages); and a precipitation step of mixing the reaction product mixture with water to precipitate the hypromellose acetate succinate.

According to the invention, the viscosity of a solution of HPMCAS in a solvent can be reduced. As a result, the viscosity of the coating composition or the composition for a solid dispersion can be reduced so that a high-concentration solution can be prepared. In addition, the amount of a solvent can be reduced so that the time required for spraying the solution onto a drug to form a coating film thereon can be reduced.

DETAILED DESCRIPTION OF THE PREFERRED EMBODIMENTS

An HPMCAS will now be described.

The HPMCAS has a degree of substitution (DS) of methyl groups of preferably 0.73 to 2.83, more preferably 1.25 to 2.37; a molar substitution (MS) of hydroxypropyl groups of preferably 0.10 to 1.90, more preferably 0.12 to 0.95; a degree of substitution (DS) of acetyl groups of preferably 0.09 to 2.30, more preferably 0.18 to 1.07; and a degree of substitution (DS) of succinyl groups of preferably 0.07 to 1.78, more preferably 0.08 to 0.62. The degree of substitution of methyl groups and the molar substitution of hydroxypropyl groups can be determined, for example, by conversion of the values obtained by the assay for hypromellose in the Japanese Pharmacopoeia Seventeenth Edition. The degree of substitution of acetyl groups and the degree of substitution of succinyl groups can be determined, for example, by conversion of the values obtained by the assay for hypromellose acetate succinate in the Japanese Pharmacopoeia Seventeenth Edition.

As described above, the substitution degree of methyl groups, the molar substitution of hydroxypropyl groups, the substitution degree of acetyl groups and the substitution degree of succinyl groups of the HPMCAS are in the same range as those of conventional HPMCAS. However, according to the invention, the environment at the site where each substituent is bonded differs from that of the conventional HPMCAS, so that the viscosity of a solution of HPMCAS in a solvent can be reduced.

A solution of 10 parts by weight of the HPMCAS in 100 parts by weight of a mixed solvent of methylene chloride and methanol at a weight ratio of 1:1 has a viscosity at 20° C. of 135 mPa·s or less, preferably 128 mPa·s or less, more preferably 110 mPa·s or less, even more preferably 100 mPa·s or less. A solution having a viscosity of more than 135 mPa·s is apt to form aggregates when sprayed onto a drug, and the resulting coating film has insufficient uniformity, thereby failing to have an intended acid resistance. A solution having a high viscosity may be difficult to supply by a pump for coating. The lower limit of the viscosity of the solution of the HPMCAS in the mixed solvent is preferably as low as possible and is preferably 50 mPa·s. The viscosity of the solution of the HPMCAS in the mixed solvent of methylene chloride and methanol can be determined by the viscosity measurement method in the Japanese Pharmacopoeia Seventeenth Edition.

The viscosity of the solution of the HPMCAS in the mixed solvent of methylene chloride and methanol has correlation with the viscosity of the solution of the HPMCAS in acetone or an aqueous ammonia solution as the solvent. Thus, it can be an index of the viscosity of the solution of the HPMCAS in acetone or an aqueous ammonia solution, which is a solvent in a coating composition or a composition for a solid dispersion.

Next, a method for producing the HPMCAS will be described.

Hypromellose (another name: hydroxypropyl methyl cellulose; hereinafter also referred to as "HPMC") as the starting material may be produced by a known method. The method, for example, comprises the steps of: bringing sheet-like, chip-like or powdery pulp into contact with an alkali metal hydroxide such as sodium hydroxide or potassium hydroxide to obtain alkali cellulose; and reacting the alkali cellulose with etherifying agents such as methyl chloride and propylene oxide to obtain the hypromellose.

The alkali metal hydroxide solution to be used may be any solution that can give alkali cellulose, and is preferably an aqueous solution of sodium hydroxide or potassium hydroxide from the standpoint of economy. The alkali metal hydroxide solution has a concentration of preferably 23 to 60% by weight, more preferably 35 to 55% by weight from the standpoint of stability of alkali cellulose and the transparency of a cellulose ether.

After the preparation of the alkali cellulose, addition of etherifying agents such as methyl chloride and propylene oxide thereto allows etherification reactions to proceed to obtain HPMC in a usual manner.

The obtained HPMC has a degree of substitution (DS) of methyl groups of preferably 0.73 to 2.83, more preferably 1.25 to 2.37. A molar substitution (MS) of the hydroxypropyl groups is preferably 0.10 to 1.90, more preferably 0.12 to 0.95. The degree of substitution of methyl groups and the molar substitution of hydroxypropyl groups may be determined, for example, by conversion of values obtained by the assay for hypromellose in the Japanese Pharmacopoeia Seventeenth Edition.

The viscosity at 20° C. of a 2% by weight aqueous HPMC solution is determined in accordance with the viscosity measurement by capillary tube viscometer in the Japanese Pharmacopoeia Seventeenth Edition, and is preferably 2.2 to 7.2 mPa·s, more preferably 3.0 to 3.5 mPa·s.

Hypromellose acetate succinate can be obtained by a production method comprising an esterification step of adding acetic anhydride and succinic anhydride as esterification agents to a solution of the above-obtained HPMC in glacial acetic acid in the presence of sodium acetate as a catalyst to obtain a reaction product mixture, and a precipitation step of mixing the reaction product mixture with water to precipitate the hypromellose acetate succinate. The hypromellose acetate succinate precipitated in the precipitation step may be subjected to optional washing and drying steps to obtain HPMCAS powder.

In the solution of the HPMC in glacial acetic acid, the amount of the glacial acetic acid is preferably 1.0 to 3.0 times, more preferably 1.2 to 2.5 times, even more preferably 1.5 to 2.0 times, particularly preferably 1.5 to 1.8 times the weight of the HPMC, from the standpoint of a reaction rate of the esterification.

In the esterification step, acetic anhydride and succinic anhydride are added to the solution of the HPMC in glacial acetic acid in the presence of sodium acetate to obtain a reaction product mixture. The method of adding the acetic anhydride is not particularly limited, and the acetic anhydride may be added at once or in portions. The timing of adding the succinic anhydride is independent of the timing of adding the acetic anhydride, but is preferably after the addition of the acetic anhydride. The succinic anhydride is added intermittently (i.e. in two or more stages). As for the method of counting the number of addition stages of the succinic anhydride, when the interval between the completion of a prior addition and the start of the subsequent addition is 4 minutes or more, the subsequent addition is regarded as being in the different addition stage from the stage of the prior addition.

The total time for adding the whole amount of succinic anhydride is preferably within 60 minutes, more preferably within 30 minutes, even more preferably within 15 minutes, from the start of the addition. The number of addition stages of succinic anhydride is preferably 2 to 14 stages, more preferably 2 to 12 stages, from the standpoint of the viscosity of a solution of the obtained HPMCAS in a solvent. Each addition stage of the succinic anhydride preferably contains continuous addition (including dropwise additions). Specifically, during a period (e.g. in each stage) when the succinic anhydride is added, the average addition rate of the succinic anhydride is preferably 0.0020 to 0.2000 mol/min, more preferably 0.010 to 0.1000 mol/min, even more preferably 0.020 to 0.0500 mol/min, from the standpoint of the viscosity of a solution of the obtained HPMCAS in a solvent. The succinic anhydride reacts with hypromellose to form a side chain of succinyl group on the hypromellose, and then the succinyl group further reacts with another hypromellose to form cross-linkage between the hypromellose molecules. By selecting the average addition rate of the succinic anhydride in a particular range, HPMCAS capable of controlling a viscosity of a solution of the HPMCAS in a solvent can be produced.

The amount of the acetic anhydride to be added is preferably 0.2 to 1.5 mol, more preferably 0.4 to 1.3 mol, even more preferably 1.1 to 1.3 mol relative to 1 mol of the reactant HPMC from the standpoint of the degree of substitution and yield of the obtained HPMCAS. The amount of the succinic anhydride to be added is preferably 0.1 to 1.0 mol, more preferably 0.1 to 0.8 mol, even more preferably 0.3 to 0.5 mol relative to 1 mol of the reactant HPMC from the standpoint of the degree of substitution and yield of the obtained HPMCAS.

The amount of the sodium acetate to be used as the catalyst in the esterification step is preferably 0.8 to 1.5 mol, more preferably 0.9 to 1.1 mol relative to 1 mol of the reactant HPMC from the standpoint of the degree of substitution and yield of HPMCAS.

For the esterification, a biaxial mixer suited for forming and kneading a highly viscous and uniform fluid mixture can be used. Examples of the mixer include a commercially available apparatus such as a kneader and an internal mixer.

The reaction temperature in the esterification step is preferably 60 to 100° C., more preferably 80 to 90° C., from the standpoint of an appropriate reaction rate or viscosity. The reaction time in the esterification step is preferably 2 to 8 hours, more preferably 3 to 6 hours.

After the esterification, optional water can be added to the reaction product mixture to decompose unreacted acetic anhydride and succinic anhydride and to control the viscosity of the reaction product mixture. The amount of water to be added is preferably 0.8 to 1.5 times, more preferably 1.0 to 1.3 times the weight of the reactant HPMC.

In the precipitation step, the obtained reaction product mixture is mixed with water to obtain hypromellose acetate succinate. The amount of water to be mixed is preferably 3.3 to 8.5 times, more preferably 3.8 to 6.5 times the weight of the reaction product mixture from the standpoint of precipitation degree and treatment time. When water is added after the esterification as described above, the amount of water to be mixed in the precipitation step is preferably 2.5 to 7.0 times, more preferably 3.0 to 5.0 times the weight of the reaction product mixture.

The temperature of water to be mixed in the precipitation step is preferably 5 to 40° C.

In the precipitation step, the temperature of the reaction product mixture just before being mixed with water is preferably 10 to 30° C., more preferably 10 to 20° C., even more preferably 15 to 20° C. In order to adjust the temperature of the reaction product mixture just before being mixed with water to the above range, cooling by a jacket of a reaction vessel may be applied.

The precipitated HPMCAS may be optionally washed and dried. In the washing and drying steps, the precipitated HPMCAS is thoroughly washed with water to remove free acetic acid and free succinic acid, and the washed precipitate is dried at preferably 60 to 100° C., more preferably 70 to 80° C., for preferably 1 to 5 hours, more preferably 2 to 3 hours. As a result, a highly pure HPMCAS can be produced.

A coating composition will next be described.

The coating composition comprises the HPMCAS and a solvent. The solvent is preferably a mixed solvent of water and an alcohol such as methanol, ethanol or isopropanol, or an aqueous ammonia solution. The mixed solvent of water and an alcohol preferably has a weight ratio of the water to the alcohol of 2:8 to 4:6. The concentration of the aqueous ammonia solution is preferably a 0.01 to 1.0% by weight.

The concentration of the HPMCAS in the coating composition is preferably 5 to 20% by weight, more preferably 7 to 15% by weight, from the standpoint of the viscosity of the solution and productivity.

A method for producing the coating composition preferably comprises a step of dissolving the HPMCAS in a solvent selected from the group consisting of a mixed solvent of water and an alcohol, and an aqueous ammonia solution.

In one of the embodiments in which an aqueous ammonia solution is used as the solvent, the HPMCAS is dispersed in water of ambient temperature, then subjected to addition of aqueous ammonia (for example, an ammonia concentration of 5 to 30% by weight) in an amount required for neutralization of the carboxyl groups in the HPMCAS, and dissolved with stirring. The ammonia to be added is preferably in the substantially equal molar amount to that of the carboxyl groups, more preferably in an amount of 80% or more of the equal molar amount, even more preferably 95 to 105% of the equal molar amount, from the standpoint of the solubility of the HPMCAS and the acid resistance of a solid preparation obtained by coating of the coating composition. When the coating composition is produced, HPMCAS is not soluble in water so that it is necessary to add an alkali for neutralization to dissolve the HPMCAS in water. When an equivalent amount of an alkali to that of the carboxyl groups in the HPMCAS is added, the HPMCAS should be neutralized and dissolved. However, if the HPMCAS is not completely dissolved by the addition of an equivalent amount of an alkali, 105% of the equivalent amount can be added.

The coating composition may optionally contain, for example, a lubricant, an additional coating base material, a plasticizer, a surfactant, a coloring agent, a pigment, a sweetener, or an antifoaming agent.

Examples of the lubricant include talc, magnesium stearate, calcium stearate, colloidal silica, and stearic acid. The talc is particularly preferred from the standpoint of prevention of adhesion between particles during coating. When a lubricant is added, the amount of the lubricant is not particularly limited as long as the effect of the invention is not impaired. The amount of the lubricant is preferably 200 parts by weight or less, more preferably 100 parts by weight or less relative to 100 parts by weight of the HPMCAS.

The additional coating base material is a coating base material other than the HPMCAS, which is an enteric base material. Examples of the additional coating base material include a water-soluble vinyl derivative such as polyvinylpyrrolidone and polyvinyl alcohol; a water-insoluble cellulose ether such as ethyl cellulose; and an acrylic or methacrylic acid copolymer such as methacrylic copolymer LD and a dispersion of an ethyl acrylate-methyl methacrylate copolymer. When an additional coating base material is added, an amount of the additional coating base material is not particularly limited as long as the effect of the invention is not impaired. The amount of the additional coating base material is preferably 100 parts by weight or less, more preferably 50 parts by weight or less relative to 100 parts by weight of the HPMCAS.

Examples of the plasticizer include citrate esters such as triethyl citrate and acetylated triethyl citrate; polyethylene glycol; propylene glycol; glycerol; glycerol fatty acid esters such as triacetin and monoacetyl glycerol; and dibutyl phthalate. When a plasticizer is added, an amount of the plasticizer is not particularly limited as long as the effect of the invention is not impaired. The amount of the plasticizer is preferably 100 parts by weight or less, more preferably 50 parts by weight or less relative to 100 parts by weight of the HPMCAS.

Examples of the surfactant include sodium lauryl sulfate, polysorbate 80, hardened oil, polyoxyethylene(105)polyoxypropylene(5) glycol (PEP101), and polyoxyethylene (160)polyoxypropylene(30) glycol. When a surfactant is added, the amount of the surfactant is not particularly limited as long as the effect of the invention is not impaired. The amount of the surfactant is preferably 30 parts by weight or less, more preferably 10 parts by weight or less relative to 100 parts by weight of the HPMCAS.

Examples of the coloring agent include yellow ferric oxide, iron sesquioxide, Food Blue No. 1, Food Blue No. 2, Food Yellow No. 4, Food Yellow No. 5, Food Green No. 3, Food Red No. 2, Food Red No. 3, Food Red No. 102, Food Red No. 104, Food Red No. 105, and Food Red No. 106. When a coloring agent is added, an amount of the coloring agent is preferably an amount commonly used in the field.

Examples of the pigment include rutile-type titanium oxide, anatase-type titanium oxide, white lead, basic lead sulfate, basic lead silicate, zinc flower, zinc sulfide, and antimony trioxide. When a pigment is added, an amount of the pigment is preferably an amount commonly used in the field.

Examples of the sweetener include aspartame, sweet hydrangea leaf, fructose, xylitol, glycyrrhizic acid or a salt thereof, saccharin, sucralose, stevia extract, white sugar, D-sorbitol, glucose, maltitol, and D-mannitol. When a sweetener is added, an amount of the sweetener is preferably an amount commonly used in the field.

Examples of the antifoaming agent include a glycerol fatty acid ester, dimethylpolysiloxane, a dimethylpolysiloxane-silicon dioxide mixture, hydrous silicon dioxide, and silicon dioxide. When an antifoaming agent is added, an amount of the antifoaming agent is preferably an amount commonly used in the field.

A composition for a solid dispersion will next be described.

The composition for a solid dispersion comprises the HPMCAS, a drug, and a solvent.

Examples of the solvent in the composition for a solid dispersion include acetone; an alcohol such as methanol, ethanol and isopropanol; an alkyl acetate such as methyl acetate and ethyl acetate; tetrahydrofuran; dichloromethane; and mixtures thereof. The acetone is preferred particularly from the standpoint of solubility.

Examples of the drug in the composition for a solid dispersion include a poorly soluble drug that has an extremely low solubility in water and is difficult to be absorbed by typical oral administration. Examples of the poorly soluble drug include drugs expressed as "practically insoluble or insoluble" and "very slightly soluble" in accordance with the Japanese Pharmacopoeia Seventeenth Edition. As described in "General Notices" in the Japanese Pharmacopoeia Seventeenth Edition, the solubility means the degree of dissolution of a drug, previously powdered in the case of a solid, within 30 minutes in a solvent at 20±5° C., by vigorous shaking for 30 seconds each time at 5-minute intervals. Here, "practically insoluble or insoluble" corresponds to such a solubility as that the amount of a solvent (water in this case) required to dissolve 1 g or 1 mL of a drug is 10,000 ml or more, and "very slightly soluble" corresponds to such a solubility as that the amount of a solvent required to dissolve 1 g or 1 mL of a drug is not less than 1,000 ml and less than 10,000 ml.

Examples of the poorly soluble drug include azole compounds such as itraconazole, ketoconazole, fluconazole and miconazole; dihydropyridine compounds such as nifedipine, nitrendipine, amlodipine, nicardipine, nilvadipine, felodipine and efonidipine; propionic acid compounds such as ibuprofen, ketoprofen and naproxen; indoleacetic acid compounds such as indomethacin and acemetacin; griseofulvin; phenytoin; carbamazepine; and dipyridamole.

A method for producing the composition for a solid dispersion comprises the steps of: providing a solution containing the HPMCAS, a drug, a solvent and an optional component such as a filler, a binder, a disintegrant, a lubricant or an aggregation inhibitor in typical amounts in the field; and removing the solvent from the solution to obtain the composition for a solid dispersion. The form of the composition for a solid dispersion can be a suspension, a homogeneous solution, or a combination of a dissolved substance and a suspended substance. The homogeneous solution in which the HPMCAS and a drug are more homogeneously dissolved is preferred.

Examples of the filler include a saccharide (such as glucose, fructose, maltose, lactose, isomerized lactose, reduced lactose, sucrose, D-mannitol, erythritol, maltitol, xylitol, palatinose, trehalose, sorbitol, cornstarch, potato starch, wheat starch, and rice starch), silicic anhydride, anhydrous calcium phosphate, precipitated calcium carbonate, and calcium silicate.

Examples of the binder include hydroxypropyl cellulose, hydroxypropyl methyl cellulose, povidone (in another name: polyvinylpyrrolidone), methyl cellulose, polyvinyl alcohol, sodium carboxymethyl cellulose, partially gelatinized starch, gelatinized starch, sodium alginate, pullulan, gum arabic powder, and gelatin.

Examples of the disintegrant include low-substituted hydroxypropyl cellulose, carmellose, carmellose calcium, sodium carboxymethyl starch, croscarmellose sodium, crospovidone, hydroxypropyl starch, and cornstarch.

Examples of the lubricant include those of the lubricant exemplified as an additive for the coating composition.

The method of removing the solvent is exemplified by a distillation-drying method and a spray-drying method. The spray-drying method widely means a method in which a solution mixture containing a poorly water-soluble drug is divided into small droplets (sprayed) and the solvent is rapidly removed from the droplets by evaporation. In preferred embodiments, droplets are mixed with a high-temperature dry gas, or an inside of a solvent-removal apparatus is kept at an incomplete vacuum pressure.

EXAMPLES

The invention will next be specifically described with reference to Synthesis Examples and Examples. It should not be construed that the invention is limited to or by them.

Example 1

In a 5-L kneader reactor equipped with a biaxial mixer, 860 g of hydroxypropyl methyl cellulose having a methyl group DS of 1.89 and a hydroxypropyl group MS of 0.24 was dissolved in 1376 g of glacial acetic acid, wherein a viscosity at 20° C. of a 2% by weight aqueous solution of the hydroxypropyl methyl cellulose was 3.38 mPa·s. Next, 415.7 g of sodium acetate was dissolved therein, and then the hydroxypropyl methyl cellulose was reacted with acetic anhydride and succinic anhydride as esterification agents at 85° C. for 5 hours. As for the additions of the esterification agents, a total of 487.3 g of acetic anhydride was added, and then 14.51 g of succinic anhydride was added in 12 stages at intervals of 5 minutes. The time of each addition stage of succinic anhydride was 1 minute, and the average addition rate of succinic anhydride was 0.034 mol/min. Then, after water was added to the reaction product mixture to stop the reaction, further water of 25° C. in an amount of 4 times the weight of the reaction product mixture was gradually added to the reaction product mixture to precipitate HPMCAS as the reaction product.

Then, the precipitate was thoroughly washed with water and dried. The dried precipitate was passed through a sieve (#7.5) having openings of 2860 μm to obtain HPMCAS having a degree of substitution (DS) of methyl groups of 1.894, a molar substitution (MS) of hydroxypropyl groups of 0.251, a degree of substitution of acetyl groups (DS) of 0.611, and a degree of substitution (DS) of succinyl groups of 0.288. The viscosity of the obtained HPMCAS was determined in a mixed solvent of methylene chloride and methanol, in acetone, or in an aqueous ammonia solution by using a measurement solution prepared by the following procedure, with a Brookfield viscometer in accordance with a viscosity measurement method described in the Japanese Pharmacopoeia Seventeenth Edition. The results are shown in Table 1.

(a) Preparation of viscosity measurement solution using a mixed solvent of methylene chloride and methanol:

In an 8-oz bottle, 45.0 g of methylene chloride and 45.0 g of methanol were placed, and stirred with a stirring blade at 200 rpm for 5 minutes. The mixture was subjected to addition of 10 g of HPMCAS, and stirred at 200 rpm for 60 minutes. Then the stirring blade was stopped, and the obtained solution was used as a measurement solution.

(b) Preparation of viscosity measurement solution using acetone as a solvent:

In an 8-oz bottle, 198.0 g of acetone was placed and was stirred with a stirring blade at 200 rpm for 5 minutes. The acetone was subjected to addition of 22 g of HPMCAS, and stirred at 200 rpm for 60 minutes. Then the stirring blade was stopped, and the obtained solution was used as a measurement solution.

(c) Preparation of viscosity measurement solution using aqueous ammonia solution as a solvent:

The 26.6 g of an HPMCAS was added to 238 g of purified water, and stirred at 300 rpm for 5 minutes to obtain a dispersion. The dispersion was subjected to addition of 3.16 g of 10% by weight aqueous ammonia solution required to neutralize the carboxyl groups in the HPMCAS, and stirred at 300 rpm for 120 minutes. Then the stirring blade was stopped, and the obtained solution was used as a measurement solution.

Example 2

HPMCAS was precipitated as the reaction product in the same manner as in Example 1 except that with respect to additions of the esterification agents, a total of 487.3 g of acetic anhydride was added, then 58.07 g of succinic anhydride was added in three stages at intervals of 30 minutes, and the time of each addition stage of succinic anhydride was 5 minutes. The average addition rate of the succinic anhydride was 0.027 mol/min. The precipitate was then thoroughly washed with water and dried. The dried precipitate was passed through a sieve (#7.5) having openings of 2860 μm to obtain HPMCAS having a degree of substitution (DS) of methyl groups of 1.845, a molar substitution (MS) of hydroxypropyl groups of 0.215, a degree of substitution (DS) of acetyl groups of 0.588, and a degree of substitution of succinyl groups of 0.285. The viscosity of the obtained HPMCAS was determined in each solvent in the same manner as in Example 1, and the results are shown in Table 1.

Example 3

HPMCAS was precipitated as the reaction product in the same manner as in Example 1 except that with respect to additions of the esterification agents, a total of 487.3 g of acetic anhydride was added, then 87.11 g of succinic anhydride was added in two stages at intervals of 60 minutes, and the time of each addition stage of succinic anhydride was 10 minutes. The average addition rate of succinic anhydride was 0.021 mol/min. The precipitate was then thoroughly washed with water and dried. The dried precipitate was passed through a sieve (#7.5) having openings of 2860 μm to obtain HPMCAS having a degree of substitution (DS) of methyl groups of 1.859, a molar substitution (MS) of hydroxypropyl groups of 0.229, a degree of substitution (DS) of acetyl groups of 0.596, and a degree of substitution (DS) of succinyl groups of 0.293. The viscosity of the obtained HPMCAS was determined in each solvent in the same manner as in Example 1, and the results are shown in Table 1.

Comparative Example 1

HPMCAS was precipitated as the reaction product in the same manner as in Example 1 except that with respect to additions of the esterification agents, a total of 487.3 g of acetic anhydride was added, and then a total of 174.21 g of succinic anhydride was added in one stage. The average addition rate of succinic anhydride was 0.410 mol/min. The precipitate was then thoroughly washed with water and dried. The dried precipitate was passed through a sieve (#7.5) having openings of 2860 μm to obtain HPMCAS powder having a degree of substitution (DS) of methyl groups of 1.848, a molar substitution (MS) of hydroxypropyl groups of 0.221, a degree of substitution (DS) of acetyl groups of 0.541, and a degree of substitution (DS) of succinyl groups of 0.359. The viscosity of the obtained HPMCAS was determined in each solvent in the same manner as in Example 1, and the results are shown in Table 1.

TABLE 1

| | addition manner of succinic anhydride | average addition rate (mol/min) | viscosity in $CH_2Cl_2$/$CH_3OH$ (mPa·s) | viscosity in acetone (mPa·s) | viscosity in aq. ammonia solution (mPa·s) |
|---|---|---|---|---|---|
| Example1 | 12 stages | 0.034 | 94.5 | 20.7 | 194.0 |
| Example2 | 3 stages | 0.027 | 126.6 | 33.2 | 295.0 |
| Example3 | 2 stages (continuous addition in each stage) | 0.021 | 131.4 | 34.8 | 358.0 |
| Comp. Ex. 1 | 1 stage | 0.410 | 1365.0 | 1370.0 | 3037.0 |

It is evident from the results in Table 1 that the viscosity in each solvent can be reduced by changing the addition manner of adding succinic anhydride.

Example 4

In a propeller mixer, 100 g of the HPMCAS produced in Example 1 was dissolved with stirring in 733 g of a mixed solvent having a weight ratio of ethanol to purified water of 8:2 for 60 minutes to obtain a coating composition having a HPMCAS concentration of 12% by weight. The viscosity at 25° C. of the coating composition was determined to be 150 mPa·s. The coating composition was capable of being fed by a tube pump (SMP-21S manufactured by EYELA).

Separately, 2 parts by weight of riboflavin (manufactured by Tokyo Tanabe Co., Ltd.), 90 parts by weight of lactose (manufactured by Freund Corporation, Dilactose S), 8 parts by weight of low-substituted hydroxypropyl cellulose (a substitution degree of hydroxypropyl groups of 11% by weight, i.e. a molar substitution (MS) of hydroxypropyl groups of 0.26), and 0.5 part by weight of magnesium stearate were mixed, and tableted with a rotary tableting machine (Virgo manufactured by Kikusui Seisakusho) at a diameter of 8 mm, a tableting pressure of 1 t, a tableting preload of 0.3 t, and a rotation rate of 20 rpm to obtain uncoated tablets, each having a weight of 200 mg.

The prepared coating composition was coated on 100 parts by weight of each uncoated tablet in the following conditions to form 7 parts by weight of coating film in terms of solid weight. The coating time was 38 minutes.

Apparatus: ventilated pan coater (inner diameter: 33 cm)
Charge amount: 1 kg
Intake air temperature: 60° C.
Discharge air temperature: 35° C.
Intake air amount: 1 m$^3$/min
Pan rotation rate: 24 rpm
Spray speed: 15 g/min
Spray air pressure: 150 kPa The 20 obtained coated tablets were subjected to the disintegration test in accordance with the Japanese Pharmacopoeia Seventeenth Edition, using 900 mL of the first fluid (pH 1.2) for the disintegration test described in the Japanese Pharmacopoeia. As a result, tablet failure such as film breakage or tablet swelling was not observed.

Subsequently, 900 mL of the second fluid (pH 6.8) for the disintegration test described in the Japanese Pharmacopoeia Seventeenth Edition, was used to perform the disintegration test in accordance with the Japanese Pharmacopoeia. As a result, it was confirmed that the drug was immediately eluted.

Comparative Example 2

In a propeller mixer, 100 g of the HPMCAS produced in Comparative Example 1 was dissolved with stirring in 733 g of a mixed solvent having a weight ratio of ethanol to purified water of 8:2 for 60 minutes to obtain a coating composition having a HPMCAS concentration of 12% by weight. The viscosity at 25° C. of the coating composition was determined to be 7,200 mPa·s. The coating composition had an excessively high viscosity so that it could not be fed by a tube pump (SMP-21S manufactured by EYELA).

Comparative Example 3

The coating liquid obtained in Comparative Example 2 could not be fed due to an excessively high viscosity, so that the HPMCAS concentration of the coating composition obtained in Comparative Example 2 was reduced so as to obtain a viscosity substantially equal to that of coating composition obtained in Example 4. Then coating was performed.

In a propeller mixer, 100 g of the HPMCAS produced in Comparative Example 1 was dissolved with stirring in 2,400 g of a mixed solvent having a weight ratio of ethanol to purified water of 8:2 for 60 minutes to obtain a coating composition having a HPMCAS concentration of 4% by weight. The viscosity at 25° C. of the coating composition was determined to be 120 mPa·s. The coating composition was capable of being fed by a tube pump (SMP-21S manufactured by EYELA).

The prepared coating composition was coated on 100 parts by weight of each uncoated tablet obtained in Example 4 in the following conditions to form 7 parts by weight of coating film in terms of solid weight. The coating time was 117 minutes.

Apparatus: ventilated pan coater (inner diameter: 33 cm)
Charge amount: 1 kg
Intake air temperature: 60° C.
Discharge air temperature: 35° C.
Intake air amount: 1 m$^3$/min
Pan rotation rate: 24 rpm
Spray speed: 15 g/min
Spray air pressure: 150 kPa It is evident from the results in Example 4 and Comparative Examples 2 and 3 that the HPMCAS obtained in Example 1 gave a coating composition with a lower viscosity than the coating composition containing the HPMCAS obtained in Comparative Example 1, so that the former coating composition could be applied at a higher concentration, thereby reducing the coating time.

The invention claimed is:

1. A method for producing hypromellose acetate succinate, the method comprising:
   an esterification step of adding acetic anhydride and succinic anhydride to a solution of hypromellose in glacial acetic acid in the presence of sodium acetate to obtain a reaction product mixture, wherein the succinic anhydride is added intermittently; and
   a precipitation step of mixing the reaction product mixture with water to precipitate the hypromellose acetate succinate,
   wherein an amount of the acetic anhydride is 0.4 to 1.3 mol relative to 1 mol of the hypromellose, and wherein a solution of 10 parts by weight of the obtained hypromellose acetate succinate in 100 parts by weight of a mixed solvent having a weight ratio of methylene chloride to methanol of 1:1 has a viscosity at 20° C. of 135 mPa.s or less.

2. The method for producing the hypromellose acetate succinate according to claim 1, wherein during a period when the succinic anhydride is added, an average addition rate of the succinic anhydride is 0.0020 to 0.2000 mol/min.

3. The method for producing the hypromellose acetate succinate according to claim 1, wherein the succinic anhydride is added at least two times, wherein the interval between each addition is 4 minutes or more.

4. The method for producing the hypromellose acetate succinate according to claim 1, wherein an amount of the glacial acetic acid is 1.2 to 2.5 times the weight of the hypromellose.

* * * * *